United States Patent [19]

Watanabe et al.

[11] 3,963,350
[45] June 15, 1976

[54] APPARATUS FOR SELECTIVELY SEGMENTING RED AND WHITE BLOOD CORPUSCLES CONTAINED IN BLOOD SMEAR

[75] Inventors: Sadakazu Watanabe, Kawasaki; Hidenori Shinoda, Yokohama, both of Japan

[73] Assignee: Tokoya Shibaura Electric Co. Ltd., Japan

[22] Filed: Nov. 12, 1974

[21] Appl. No.: 523,056

[30] Foreign Application Priority Data
Nov. 13, 1973 Japan.............................. 48-126782

[52] U.S. Cl.................................. 356/39; 356/201
[51] Int. Cl.² ................. G01M 33/16; G01N 21/06
[58] Field of Search.............................. 356/39, 201

[56] References Cited
UNITED STATES PATENTS

| | | | |
|---|---|---|---|
| 2,875,666 | 3/1959 | Parker et al. | 356/39 |
| 3,684,377 | 8/1972 | Adams et al. | 356/39 X |
| 3,714,372 | 1/1973 | Rosen et al. | 356/39 |
| 3,824,393 | 7/1974 | Brain | 356/39 X |

*Primary Examiner*—Robert Segal
*Attorney, Agent, or Firm*—Cushman, Darby & Cushman

[57] ABSTRACT

The segmentation apparatus comprises means for illuminating a blood smear mounted on a slide and subjected to WRIGHT staining successively with lights having wavelengths of 410 nm and 530 nm respectively for obtaining two blood corpuscle images produced by monochromatic lights having respective wavelengths, means for producing two electric signals having levels corresponding to the tones of respective blood corpuscle images, means for converting the two electric signals into binary signals in accordance with two different threshold valves, means for obtaining the exclusive OR of the two binary signals for detecting the white blood corpuscles in the blood, and means for obtaining the logical product of said two binary signals the segmenting the red blood corpuscles in the blood.

6 Claims, 12 Drawing Figures

RED CORPUSCLES

WHITE CORPUSCLE

RED CORPUSCLE

WHITE CORPUSCLE

APPARATUS FOR SELECTIVELY SEGMENTING RED AND WHITE BLOOD CORPUSCLES CONTAINED IN BLOOD SMEAR

BACKGROUND OF THE INVENTION

This invention relates to apparatus for selectively segmenting white blood corpuscles and red blood corpuscles in blood.

Clinical examination of blood usually performed includes hematrocrit measurement, hemoglobin measurement, counting of the number of red blood corpuscles, counting of the number of white blood corpuscles, counting of the number of serums, counting of the number of the reticulocytes and identification and counting of the number of white blood corpuscles. Of these number of methods since the method of calculating the number of the reticulocytes and the method of identifying and calculating the number of white blood corpuscles require to identify the form of pattern of the reticulocytes and white blood corpuscles it is extremely difficult to perform such examinations by automatic apparatus.

In order to identify the pattern of a blood corpuscle image it is necessary to firstly segment a desired blood corpuscle image. For example, for the purpose of discriminating white blood corpuscles it is necessary to remove the red blood corpuscles from blood corpuscles containing both red and white blood corpuscles and then to obtain the image of only the white blood corpuscles. Since the result of detection and segmentation of specific type of the blood corpuscles directly influences the result of discrimination, development of improved segmentation means has long been desired.

According to one prior method a medicament is added to blood comprising a mixture of red and white blood corpuscles for the purpose of chemically destroying the red blood corpuscles along. According to this method, however, some of the white blood corpuscles in the sample are also deformed. Further, as it is necessary to stain the sample after incorporation of the medicament the form of the resulting sample becomes different from the standard form presently used widely so that there is an inconvenience that it is necessary to prepare again the sample for the next observation. Further, this method is difficult to completely remove the red blood corpuscles thus leaving some of them. This results in an error in the calculated number of the white blood corpuscles.

According to another method, use is made of a three filters corresponding to three primary colors, wherein respective picture elements of the blood corpuscle image which are obtained by the analytic action of the three primary colour filter are displayed as spots in a three dimentional vector space so as to discriminate the white and red blood corpuscles according to the positions of the spots in said space. According to this method although it is possible to preserve the form of ordinary samples it is necessary to use a large capacity memory device capable of storing various tones of respective images corresponding to respective dimensions produced by the three primary color filter. Moreover, as it is necessary to use a high speed digital-analogue converter for the memory device the apparatus is bulky and expensive.

SUMMARY OF THE INVENTION

Accordingly, it is an object of this invention to provide an improved apparatus capable of readily, rapidly, correctly and selectively segmenting the red blood corpuscles and white blood corpuscles contained in blood by using a sample of the standard form now being widely used thereby obtaining desired data concerning blood corpuscle images.

Another object of this invention is to provide a novel apparatus for discriminating the red and white blood corpuscles capable of reducing the capacity of the memory device usually used for this purpose, thereby reducing the size and cost of the apparatus.

In accordance with this invention these and other objects can be accomplished by providing apparatus for selectively segmenting red blood corpuslces and white blood corpuscles contained in blood, comprising means for illuminating stained blood smears mounted on a slide with monochromatic light having any wavelength between 400 nm and 430 nm and with monochromatic light having any wavelength between 500 nm and 560 nm for obtaining blood corpuscle image for respective monochromatic lights, means for scanning respective blood corpuscle images and photoelectrically converting the result of scanning into electric signals corresponding to the tones of respective blood corpuscle images, means for converting the electric signals into binary signals in accordance with two threshold values having predetermined levels, and means responsive to one binary signal corresponding to one monochromatic light and to the other binary signal corresponding to the other monochromatic light for selectively segmenting and isolating red and white blood corpuscles contained in the blood.

DESCRIPTION OF THE PREFERRED EMBODIMENT

Figure 1A:
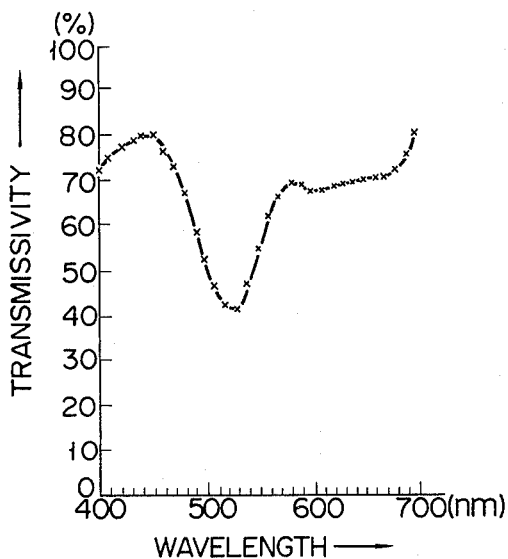
FIGS. 1A to 1D are graphs showing absorption spectral characteristics for visible lights of various types of the blood corpuscles contained in blood.

In the accompanying drawings, FIGS. 1A through 1D show absorption spectral characteristics for visible lights of special portions of red blood corpuscles and white blood corpuscles subjected to so-called WRIGHT staining. In these figures the abscissa represents the wavelength and the ordinate transmissivity of the light. FIG. 1A shows the absorption spectral characteristic of the cellular substance of the white blood corpuscles, FIG. 1B that of the nuclei of the white blood corpuscles, FIG. 1C that of the red blood corpuscles and FIG. 1D that of the background which is a slide utilized in microscopes. WRIGHT STAIN is a method of staining blood corpuscles. Other methods of dyeing commonly used include WRIGHT-GIEMSA stain and MAY-GRUNDWALD STAIN.

Figure 1B:
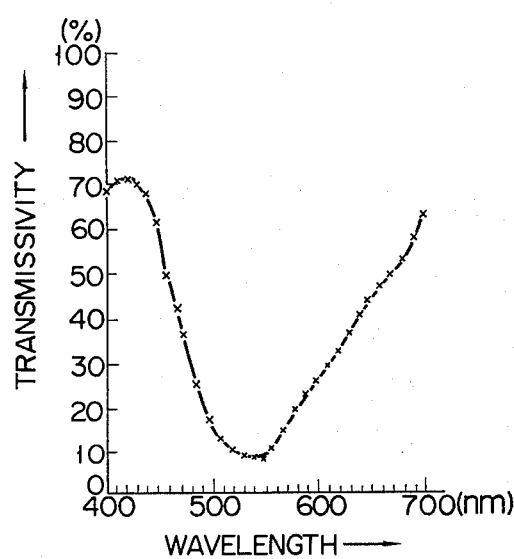
Figure 1C:
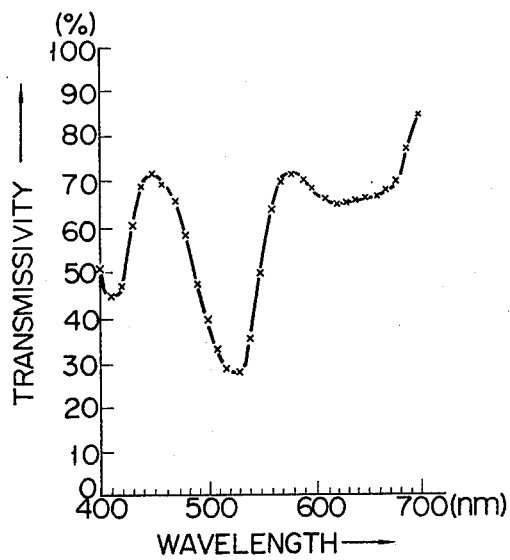
Figure 1D:
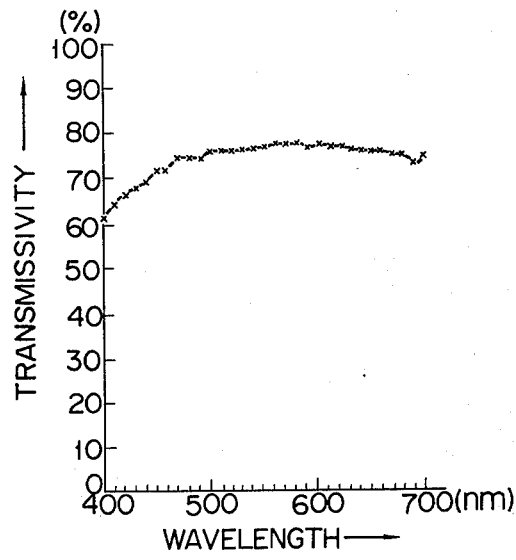

As can be clearly noted from FIGS. 1A and 1B the white blood corpuscles shows a maximum absorption only near 530 nm whereas as FIG. 1C shows the red blood corpuscles show remarkable adsorption near 410 nm and 530 nm. The invention contemplates unique utilization of the difference in the absorption characteristics of the white and red blood corpuscles for selectively segmenting and isolating these two types of the blood corpuscles.

More particularly, the microscopic image of the blood corpuscles on a slide irradiated with a monochromatic light having a wavelength of 530 nm is picked up by an image pick up tube for forming a video signal. Since both red and white blood corpuscles exhibit an intense absorption characteristic for the light having a wavelength of 530 nm, the level of the video signal decreases greatly for red and white blood corpuscles. As a consequence, it is possible to obtain bindary images for only red and white blood corpuscles by using a predetermined signal level including such decreased portions a threshold value, comparing the level of the video signal with the threshold value, expressing the higher level by a binary 0 and the lower level by a binary 1 and then reproducing the binary video signal. Thereafter, the blood corpuscles on the slide are irradiated with a monochromatic light having a wavelength of 410 nm to form a video signal of the micrographic image thereof. As shown in FIG. 1C, since only the red blood corpuscles manifest an intense absorption characteristic for the light having a wavelength of 410 nm the level of the video signal decreases greatly only at the portion of the red blood corpuscles. Accordingly, it is possible to obtain a binary image for only the red blood corpuscles by using a predetermined level containing the decreased portion as a threshold value, comparing the level of the video signal with the threshold value expressing a higher level by a binary 0 and a lower level by a binary 1 and then reproducing the binary video signal. Where a logical product of a binary signal obtained by using light having a wavelength of 530 nm and a binary signal obtained by using light having a wavelength of 410 nm a signal for only the red blood corpuscles can be obtained whereas the exclusive OR of said two binary signals represents only the white blood corpuscles. This can be shown by the following logical equations.

$$P(410) \cdot P(530) \ldots \ldots \quad (1)$$

$$P(410) \; P(530) \ldots \ldots \quad (2)$$

where P represents binary image data, the numeral in the parentheses represents the wavelength (nm) of the monochromatic lights, a symbol representing a logical product and a symbol representing an exclusive OR.

Figure 2:
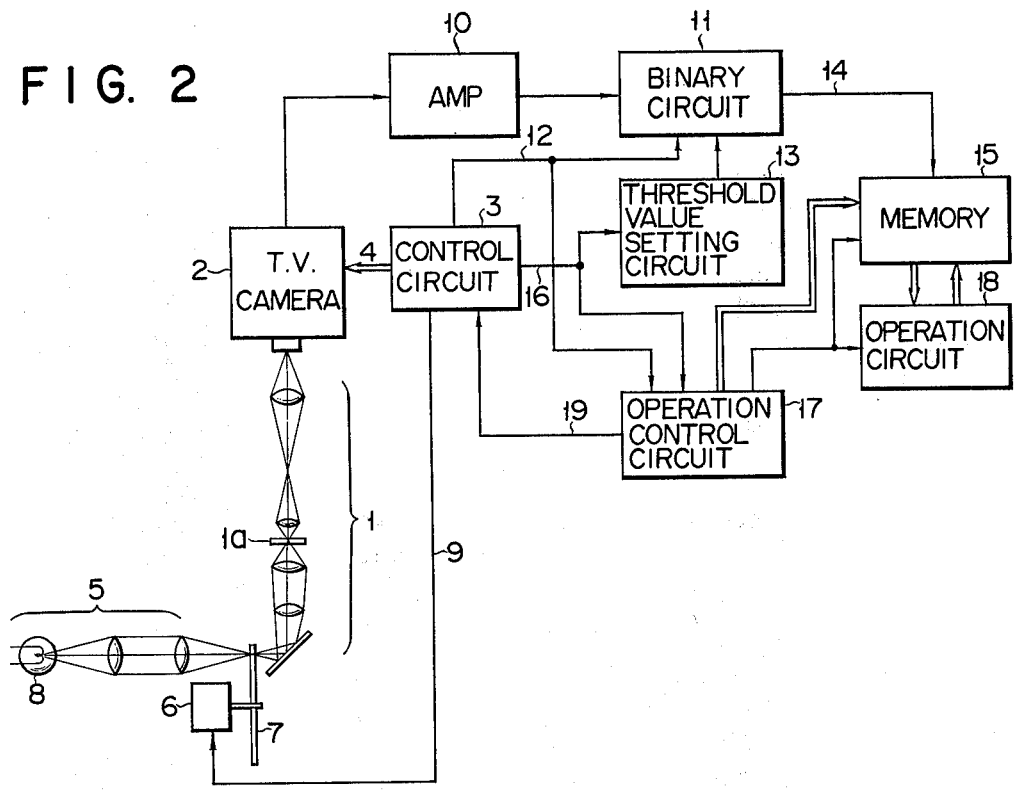
FIG. 2 is a block diagram showing one embodiment of this invention.

Referring now to FIG. 2 which shows a preferred embodiment of the novel apparatus for selectively segmenting and isolating red and white blood corpuscles according to the principle of this invention, a slide 1a is mounted on a stage of a microscope 1, only the optical system thereof being shown for simplicity. The slide 1a supports a WRIGHT-stained blood smear, for example, and the microscopic image of the sample is focused on the face plate of the image pickup tube of a television camera 2 which is controlled by a control circuit 3 through a group of control wires 4 in a manner to be described later in detail. The group of control wires 4 is used to apply synchronizing signals, blanking signals, etc., to the television camera 2.

The slide 1a is illuminated from under monochromatic light having a predetermined wavelength and supplied by an illuminating system including a lamp 8. The monochromatic light is obtained by passing the light emitted by the lamp 8 through a filter 7 rotated by a pulse motor 6. The filter 7 comprises an interference filter constructed to produce monochromatic lights of continuously changing wavelength over a wavelength of range of 400 nm to 700 nm in accordance with the angular position thereof and may be a circular variable visible filter (trade name) sold by Optical Coating Laboratory Incorporated (OCLI). The pulse motor 6 is rotated stepwisely by pulse applied thereto from the control circuit 3 through a conductor 9 such that the wavelength of the filter output varies successively at an interval of 10 nm.

Let us assume that the filter 7 assumes a position at which monochromatic light having a wavelength of 400 nm is produced. Accordingly, the microscopic image of the blood smear illuminated by the 400 nm monochromatic light is picked up by the television camera 2 and converted into a video signal. After being amplified by a video signal amplifier 10, the video signal is applied to a binary circuit 11 in which the video signal is converted into a binary signal by a sampling pulse sent from the control circuit 3. Since the control circuit 3 is constructed such that it sends the sampling pulse to the binary circuit 11 only when monochromatic lights having wavelengths of 410 nm and 530 nm are used, where monochromatic light having a wavelength of 400 nm is used, the video signal is not converted into a binary signal. The binary circuit 11 may be constituted by Schmidt circuits. Where monochromatic light having a wavelength of 400 nm is used, upon completion of the image pickup operation, the control circuit 3 sends one pulse to the pulse motor 6 through conductor 9 thus advancing filter 7 one step to the position of 410 nm. The image of the blood corpuscles illuminated by the monochromatic light having a wavelength of 410 nm is applied to the binary circuit 11 through amplifier 10 and then sampled by the sampling pulse sent from control circuit 3 through a conductor 12. The video signal sampled in this manner is converted into a binary signal in accordance with a threshold value which is predetermined according to the wavelength of 410 nm and sent from a threshold value setting circuit 13. The threshold value has a level proportioned to detect only the red blood corpuscles as described above. The binary signal is supplied to a memory device 15 through a conductor 14 and stored in the memory device 15. When all binary signals concerning $n \times m$ sampling points in a predetermined area of the slide are stored in the memory device 15, the control circuit 3 sends again a pulse signal to step motor 6 thus setting the filter 7 to a wavelength of 420 nm. At this time, since no sampling pulse is generated by the control circuit 3, the video signal will not be converted into a binary signal nor stored in the memory device 15. In the same manner, until a wavelength of 530 nm is reached no sampling pulse is generated and no binary signal is formed. However, when the filter 7 is set to a wavelength of 530 nm the control circuit 3 sends a sampling pulse to the binary circuit 11 and the sampled video signal is converted into a binary signal in accordance with a threshold value signal which is predetermined to correspond to the wavelength of 530 nm and sent from the threshold value setting circuit 13. As has been pointed out before, the level of the threshold value is determined such that sufficiently large contrast for the background formed by the slide can be obtained and that both red and white blood corpuscles can be segmented. The video signal converted into a binary signal is stored in the memory device 15 in the same manner as in the case of the 410 nm light. Furthermore, the control circuit 3 sends an information regarding a particular wavelength at which the filter 7 is presently sent to the threshold value setting circuit 13 and an operation control circuit 17 through a conductor 16. Although in this embodiment, two filters for the wavelengths of 410 nm and 530 nm are selected out of a plurality of filters for different wavelengths by using the sampling pulse, the arrangement can be simplified if only two filters are selectively used.

The binary signals of the video signals produced by using two filters for specific wavelengths of 410 nm and 530 nm are then sent to an operation circuit 18 from the memory device 15 under the control of the operation control circuit 17. As will be described later in detail, the operation circuit 18 is constructed to operate the logical product expressed by the equation (1) when it is desired to segment and isolate only the red blood corpuscles whereas to operate the exclusive OR expressed by the equation (2) where it is desired to segment and isolate only the white blood corpuscles.

The construction of the control circuit 3 will now be described with reference to FIG. 3. Thus, a clock pulse generator 311 generates a pulse having a period of 1/N of 63.5 microseconds, which is the horizontal scanning period of the television camera 2. This pulse having a period of 63.5/N microseconds is applied to an N step counter 312. Accordingly, the counter 312 returns to its 0 position at a period of 63.5 microseconds and provides a carry signal acting as a horizontal synchronizing signal to the television camera 2 over a conductor 4-2. The carry signal from the counter 312 is applied to an M step counter 313 and countered thereby. Since the number M is set to be equal to the number of the horizontal scanning lines in one field of the television system the counter 313 returns to the 0 state with a period of 63.5 × M microseconds and produces a carry signal acting as a vertical synchronizing signal, which is also sent to the television camera 2 over a conductor 4-3.

It is necessary to apply blanking signals before and after the horizontal and vertical synchronizing signals and such blanking signals are formed by comparators 314a, 314b, 315a and 315b and registers 316, 317, 318 and 319. For example, if the blanking periods before and after the horizontal synchronizing signal are set to be equal to a length corresponding to 10 clock pulses generated by the clock pulse generator 311, 10 clock pulses (from N-10 to N-1) immediately preceding the carry signal or the horizontal synchronizing pulse produced by the counter 312 will correspond to the blanking period immediately preceding the horizontal synchronizing pulse. Similarly 10 clock pulses (0 to 9) immediately following the carry signal produced by the counter 312 correspond to the blanking period immediately following the horizontal synchronizing pulse. Accordingly, as shown in FIG. 3 by comparing by means of a comparator 314b the count of from N-10 to N-1 of the counter 312 with the output from the register 317 in which a content corresponding to said count has been set, the immediately preceding blanking signal can be produced on the conductor 4-1. Further, the register 316 has been storing a content corresponding to the counter of from 0 to 9 of the counter 312 so that by comparing the content of counter 312 with the content from the register 316 by means of the comparator 314a, it is possible to produce the immediately following blanking signal on a conductor 4-1.

In the same manner as the horizontal synchronizing pulse, the blanking signal immediately after the vertical synchronizing signal is formed by a register 318 and the comparator 315a, whereas the blanking signal immediately preceding the vertical synchronizing pulse is formed by the register 319 and the comparator 315b, and these blanking signals are sent to the television camera 2 shown in FIG. 1 over a conductor 4—4.

The vertical synchronizing pulse from the counter 313 is also sent to a counter 331 and to the pulse motor 6 shown in FIG. 2 over the conductor 9. Thus, the pulse motor 6 rotates one step in response to the vertical synchronizing pulse which is sent to the motor 6 whenever one frame scanning of the television system is completed. The counter 331 is a 31 step counter which produces a carry signal when it counts 31 vertical synchronizing signals of 0 to 30 and at the same time returns to its 0 state. One vertical synchronizing signal rotates the pulse motor 6 one step to vary the wavelength of the output light from the filter 7 by 10 nm so that the counts 0 through 30 of the counter 331 represent numbers respectively corresponding to the wavelengths of the filter 7. Thus for example, count 1 corresponds to a wavelength of 410 nm and count 13 to a wavelength of 530 nm. A decoder 332 is connected to the output of the counter 331 for sending a binary 1 signal to conductors 16-1 and 16-2, respectively when the content of the counter 331 reaches 1 and 13, respectively. This 1 signal is applied to one input of an AND gate circuit 322 through an OR gate circuit 335 and a conductor 25. To the other input of the AND gate circuit 322 is applied a clock pulse through inverters 336 and 337 and AND gate circuits 338 and 321 when there is no blanking signal for the horizontal and vertical synchronizing signals. As a consequence, a sampling pulse is sent to the binary circuit 11 shown in FIG. 2 via the conductor 12 only when there is no horizontal and vertical blanking signals and the content of the counter 331 reaches 1 or 13.

When a signal is applied to the reset terminal of a flip-flop circuit 333 from the operation control circuit 17 via a conductor 19, the flip-flop circuit 333 is reset thus indicating that the operation has been completed and that blood corpuscles have been detected. Accordingly, apparatus for determining the position and shape of the detected blood corpuscles may be constructed to operate in response to the set and reset states of the flip-flop circuit 333.

Figure 3:
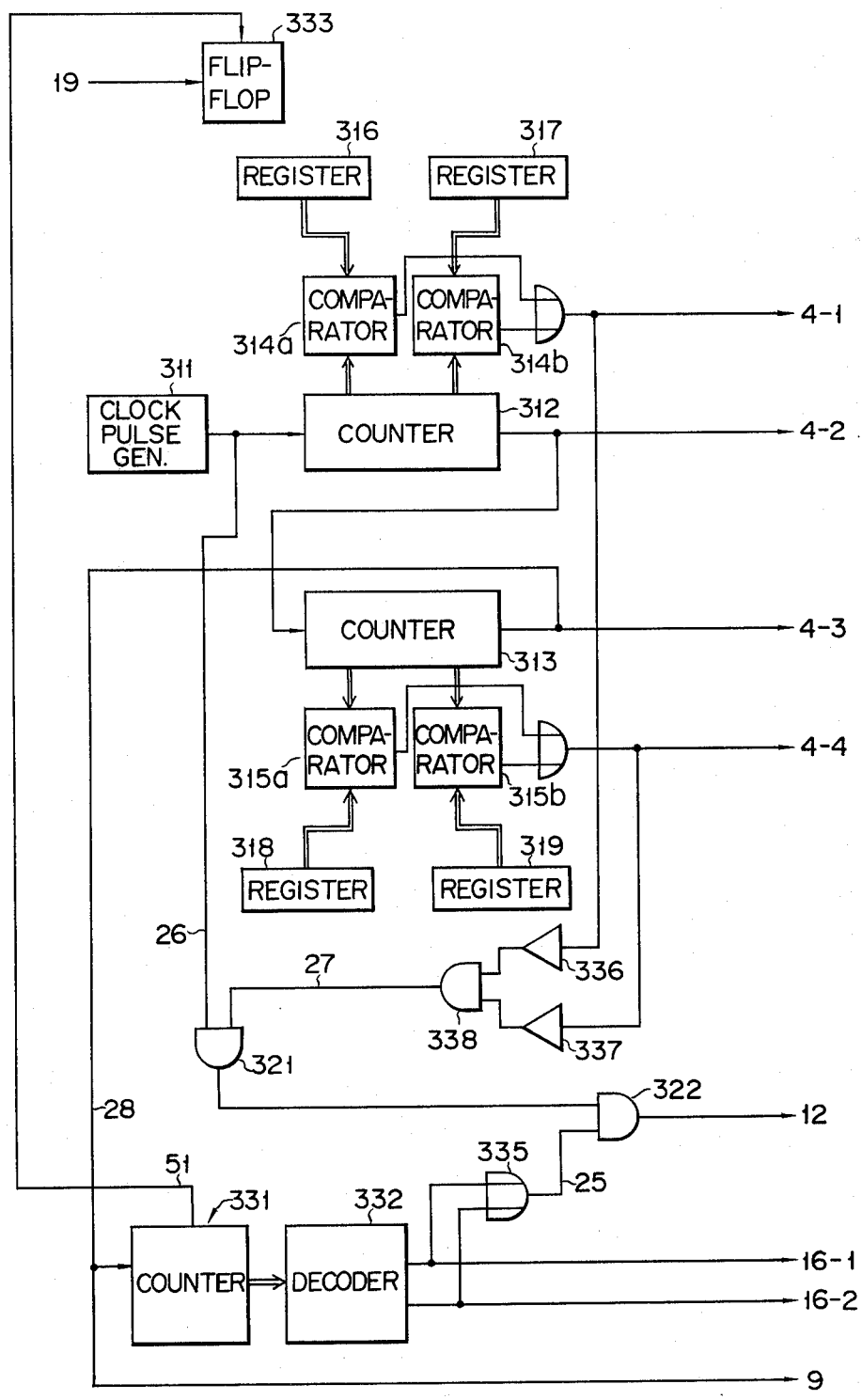
FIG. 3 is a block diagram showing the detail of the construction of the control circuit shown in FIG. 2.
Figure 4:
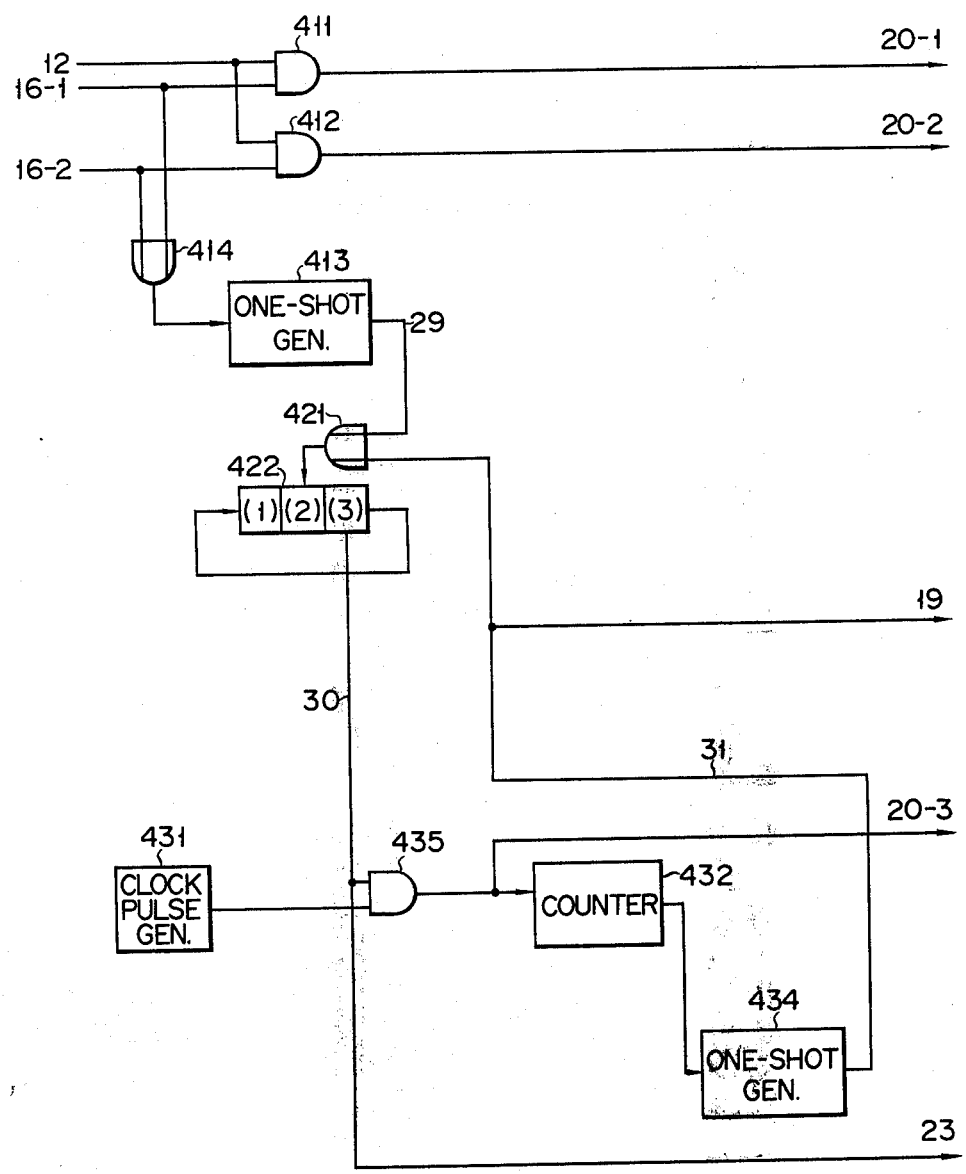
FIG. 4 is a block diagram showing the detail of the construction of the operation control circuit shown in FIG. 2.
Figure 6A:
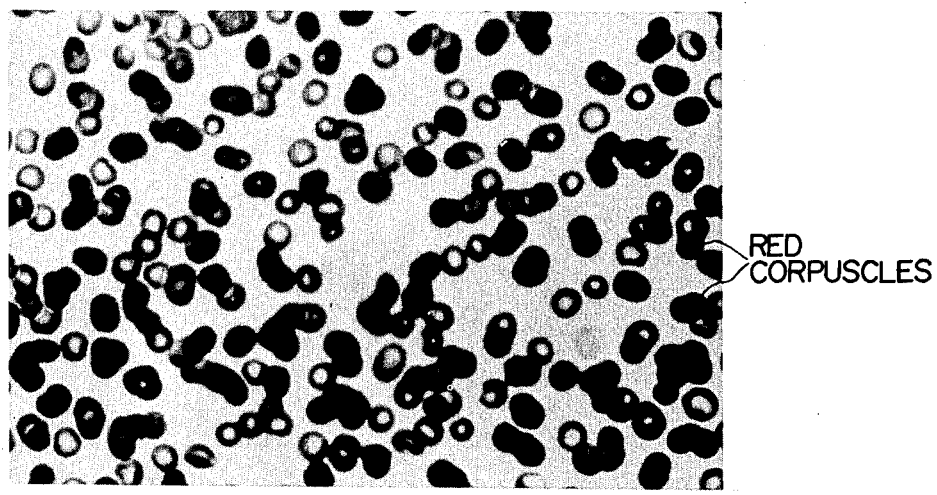
FIGs. 6A through 6D are microphotographs respectively showing images of blood corpuscles respectively illuminated by monochromatic lights having wavelengths of 410 nm, 430 nm, 450 nm and 530 nm.
Figure 6B:
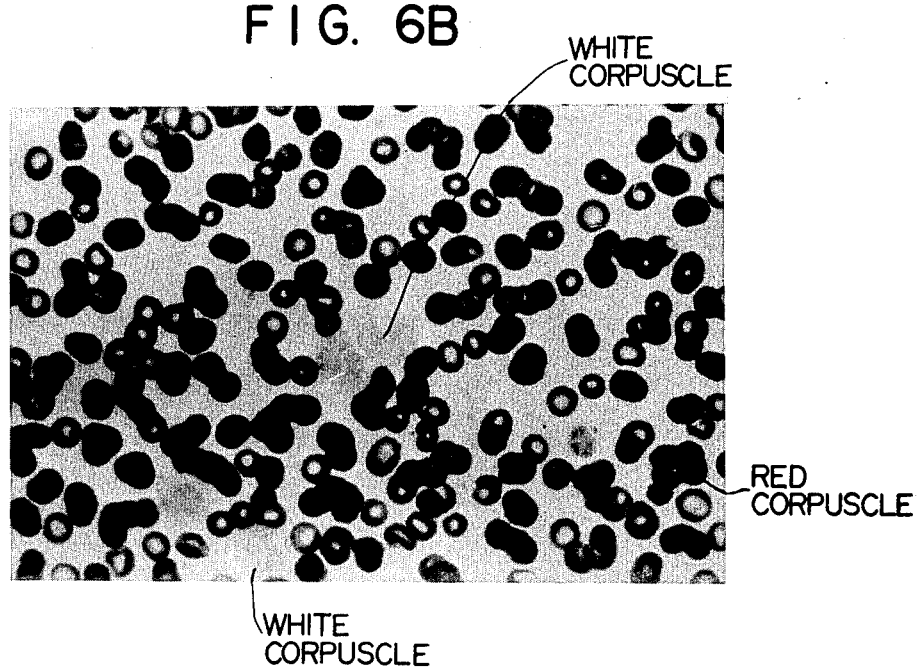
Figure 6C:
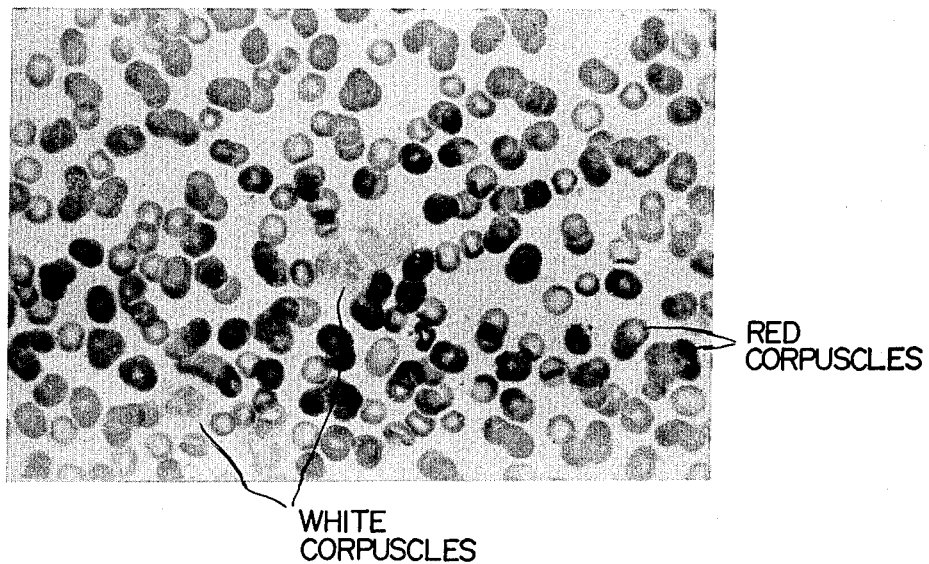
Figure 6D:
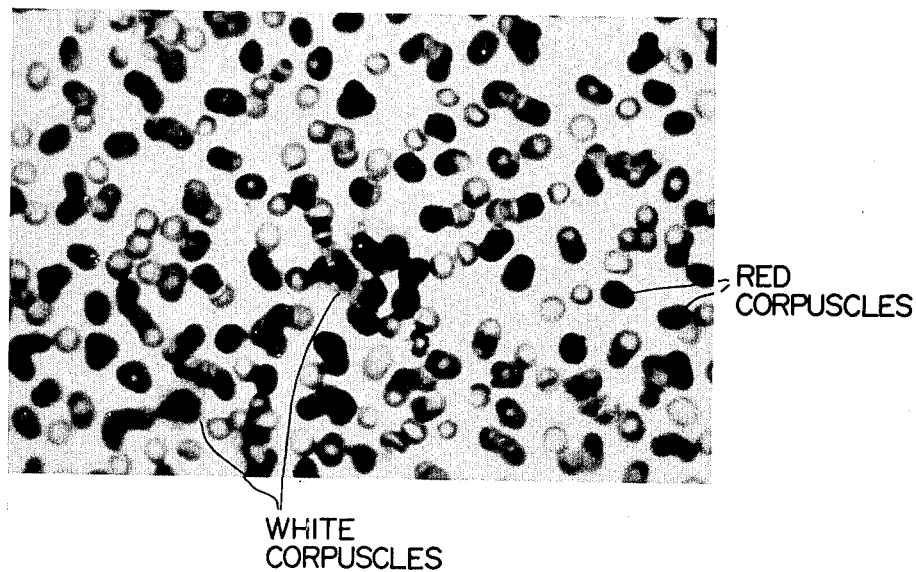

The detail of the operation control circuit 17 is shown in FIG. 4 in which the outputs from the AND gate circuit 322 in FIG. 3 are applied to the inputs of AND gate circuits 411 and 412. These AND gate circuits 411 and 412 send their outputs to the memory device 15 over conductors 20-1 and 20-2 at a rate of the clock pulse when there is a sampling pulse and when the content of the counter 331 is equal to 1 or 13. Further, the output from the decoder 332 is applied to a one-shot generator 413 through an OR gate circuit 414, which is constructed to produce a pulse when the output from the decoder 332 changes from 1 to 0 state. This pulse is applied to the shift terminal of a ring counter 422 through an OR gate circuit 421 to act as a shift pulse. The ring counter 422 comprises three bits, one of them being 1 and others 0. At first the bit (1) of the ring counter 422 is set to 1 and when the detection of the lights having wavelengths of 410 nm and 530 nm, respectively is finished, the ring counter 422 is successively shifted and when the content of bit 3 is changed to 1 state the ring counter 422 generates a signal that enables an AND gate circuit 435 to send the clock pulse from a clock pulse generator 431 to a counter 432 and to a conductor 20-3 via the AND gate circuit 435. The conductor 20-3 is used to apply a clock pulse to the memory device 15 which acts as a shift pulse that shifts tje o,age pf tje ,e,pru ,ade bu sjoft registers. The 1 signal from the bit 3 of the ring counter 422 is also sent to the memory device 15 and to the operation circuit 18 over a conductor 23 to act as an operation commencing command signal.

Counter 432 is an $m$ step counter corresponding to the total number $m$ of the bits in one line shift register of the memory device 15 so that as the count of the counter 432 reaches m—1, the desired blood cells will be detected in the register group 55 of the memory device 15. When the counter 432 counts $m$ clock pulses to produce a carry signal, this carry signal is sent to a one-shot generator 434 which generates a pulse in response to the trailing or build-down edge of the carry signal generated by the counter 432. This pulse is sent to the flip-flop circuit 333 shown in FIG. 3 over the conductor 19 to reset the flip-flop circuit 333 thus representing the finishing of the operation. This pulse is also applied to the ring counter 422 through the OR gate circuit 421 to act as a shift pulse. In response to this shift pulse, the 1 signal in bit 3 of the ring counter 422 is shifted to bit 1 thus restoring the state of commencing the detection.

Figure 5:
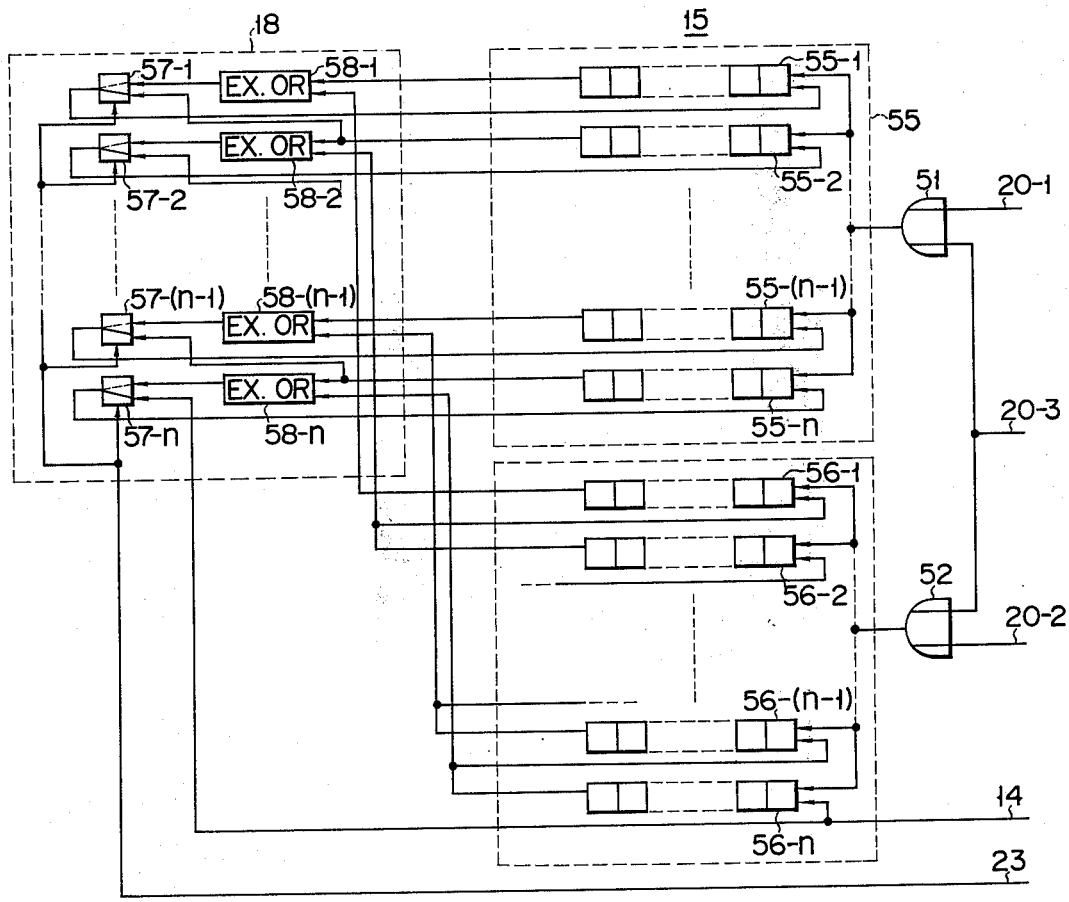
FIG. 5 is a block diagram showing the detail of the construction of the memory and operation circuits shown in FIG. 2.

Referring now to FIG. 5, the output conductors 20-1 and 20-2 shown in FIG. 4 are connected to respective one inputs of OR gate circuits 51 and 52, whereas the output conductor 20-3 is connected to the other inputs of these OR gate circuits 51 and 52 while the filter 7 is set to the light having a wavelength of 410 nm, the shift signals transmitted over the conductor 20-1 is applied to one group of registers 55-1, 55-2, . . . 55—(n-1) and 55-n of the memory device 15 through the OR gate circuit 51, whereas when the filter 7 is set to the light having a wavelength of 530 nm, shift signal transmitted over the conductor 20-2 is applied to the other group of registers 56-1, 56-2, . . . 56—(n-1) and 56-n of the memory device 15 via the OR gate circuit 52. At first a binary information for 410 nm is sent to the memory device 15 through a conductor 14. At this time, since the bit 1 of the ring counter 422 shown in FIG. 4 is at 1 state and the bit 3 is at 0 state the selection gates 57-1, 57-2, . . . 57—(n- 1) and 57-n of the operation circuit 18 are connected as shown by solid lines. Accordingly, the binary signal for 410 nm sent over the conductor 14 is firstly applied to the register 55-n through the selection gate 57-n. When this register 55-n reaches its full state, the binary signal is applied to the register 55—(n-1) of the higher order through the selection gate 57—(n-1). In the same manner, the binary signal for a wavelength of 410 nm is stored successively in the register group 55 through selection gates 57-n through 57-1.

When the filter 7 is set to the light having a wavelength of 530 nm, the shift signal from the conductor 20-2 is applied to the registers 56-1 to 56-n through the OR gate circuit 52. Again since the bit 2 of the ring counter 422 is at 1 state and the bit 3 is at 0 state the selection gates 57-1 through 57-n are maintained in the solid line positions. However, as the register group 55 is not supplied with the shift pulse, the binary signal for 530 nm recieved from the conductor 14 is applied to the lowermost register 56-n of the register group 56. In the same manner as has been described in connection with the wavelength of 410 nm, the binary signal for 530 nm is stored successively in the register group 56.

When the binary data regarding the blood corpuscle image obtained by setting the filter 7 to 410 nm are stored in the register group 55 and when the binary data regarding the blood corpuscle image obtained by setting the filter 7 to 530 nm are stored in the register group 56 in a manner described above, the content of the bit 3 of the ring counter 422 shown in FIG. 4 changes to 1 state and this 1 signal is applied to the selection gates 57-1 through 57-n through the conductor 23 to act as the operation performing command signal with the result that the selection gates 57-1 through 57-n will be connected as shown by dotted lines. Under these conditions, the AND gate circuit 435 shown in FIG. 4 applies a shift pulse simultaneously to the OR gate circuits 51 and 52 through the conductor 20-3 thereby simultaneously shifting the binary data stored in the register groups 55 and 56 by one bit respectively towards left. As a result the data in the register 55-1 and the data in the corresponding register 56-1 are simultaneously sent to an excluse OR gate circuit 58-1 at the uppermost stage of the operation circuit 18, whereby the logical operation of the equation 2 is executed. In the same manner, the contents of the corresponding registers in groups 55 and 56 are successively sent to exclusive OR gate circuits 58-2 through 58-n thus indivisually executing the operation of the equation 2. The results of the operations are again stored in the respective registers in the group 55 through selection gates 57-1 through 57-n. Although in this embodiment, the number of registers has been decreased by storing again the result of the exclusive OR operations in the register group 55, it should be understood that the results of the operations may be stored in the additional registers. The selection gates can be readily fabricated by using AND gate circuits, and any one of well known exclusive OR gate circuits may be used.

As described above, the exclusive OR of the blood corpuscle image data obtained by illuminating the sample with light having a wavelength of 410 nm and the blood corpuscle image data obtained by illuminating the sample with light having a wavelength 530 nm is obtained so that the segmented data regarding the white blood corpuscles alone are stored in the register group 55.

Where it is desired to segment only the red blood corpuscles the exclusive OR gate circuits 58-1 through 58-n are substituted by AND gate circuits. If the contents of the register groups 55 and 56 are sent in parallel to the exclusive OR gate circuits and the AND gate circuits it would be possible to simultaneously obtain the data regarding the white and red blood corpuscles.

Since in this invention it is necessary to use only two register groups for two fields of the television system as the memory device 15, it is possible to greatly reduce the capacity of the memory device than the prior art apparatus utilizing three primary colour filter, whereby the apparatus can be simplified.

Although in the above described embodiment the desired blood corpuscle images were obtained by using most suitable wavelengths of 410 nm and 530 nm as a result of comparing the absorption spectral characteristics of white and red blood corpuscles shown in FIGS. 1A through 1D, we have confirmed by experiments that the same satisfactory result can be obtained by using light having a wavelength between 400 nm and 430 nm.

FIGS. 6A through 6D show micrographs of blood corpuscle images when the sample was illuminated by the lights having wavelengths of 410 nm, 430 nm, 450 nm and 530 nm respectively. At these micrographs show, with the wavelength of 450 nm, there is no appreciable difference in the contracts of the images of white and red blood corpuscles, so that it is difficult to segment and independently detect red and white blood corpuscles. However, in FIG. 6D, the difference in the contrasts of the images of the red and white blood corpuscles is large. But with the light having wavelengths shorter than 500 nm and longer than 560 nm the difference in the contrasts decreases. For this reason, it is possible to obtain the desired data by using monochromatic lights having wavelengths between 400 nm and 430 nm and between 500 nm and 560 nm.

What we claim is:

1. Apparatus for selectively segmenting red blood corpuscles and white blood corpuscles contained in blood, said apparatus comprising means for illuminating stained blood smears mounted on a slide with monochromatic light having a first wavelength between 400 nm and 430 nm and with monochromatic light having a second wavelength between 500 nm and 560 nm for obtaining blood corpuscle first and second images for said respective monochromatic wavelengths, means for scanning said respective blood corpuscle images and photoelectrically converting the result of scanning into first and second electric signals corresponding to the transmitted light of the respective blood corpuscle images at first and second wavelengths, means for converting said first and second electric signals into binary signals in accordance with two threshold values having predetermined levels, and means responsive to one binary signal corresponding to one monochromatic wavelength and to the other binary signal corresponding to the other monochromatic wavelength for carrying out first and second logical operations on said binary signals so as to selectively segment and isolate the data of the red and white blood corpuscles contained in the blood.

2. Apparatus for selectively segmenting red blood corpuscles and white blood corpuscles contained in blood, comprising means for illuminating stained blood smears mounted on a slide successively with monochromatic lights having any wavelengths between 400 and 430 nm and between 500 and 560 nm, respectively, for obtaining microscopic blood corpuscle images of respective monochromatic light images, a television camera for photographing said microscopic images to form video signals, circuit means for converting said video signals into two binary signals in accordance with two threshold values having predetermined levels, a threshold value setting circuit for applying said threshold values to said circuit means, a control circuit for controlling the operations of said television camera and said threshold value setting circuit, a memory device including first and second register groups for storing said two binary signals respectively, operation means for operating the exclusive OR operation and the logical product operation of the two binary signals stored in said first and second register groups, and operation control means for controlling the operation of said operation means, whereby the data regarding only the white blood corpuscle image in the blood are detected by said exclusive OR operation and the data regarding only the red blood corpuscle image are segmented by said logical product operation.

3. The apparatus according to claim 2 wherein said control circuit comprises a clock pulse generator for producing a clock pulse having a period equal to 1/N of one horizontal scanning period of a television system, a first counter for counting N clock pulses to produce a first carry signal, a second counter for counting M first carry signal, produced by said first counter for producing a second carry signal, where M is equal to the number of the horizontal scanning lines in one frame of said television system, circuit means associated with said first and second counters for adding blanking signals immediately before and after the respective carry signals, means for applying to said television camera the output from said circuit means and said first and second carry signals produced by said first and second counters respectively to act as the blanking signal and as the horizontal and vertical synchronizing signals, a third counter for counting the number of said second carry signals produced by said second counter, a decoder for producing outputs when the count of said third counter reaches values respectively corresponding to the lights having wavelengths of 410 nm and 530 nm respectively, and means responsive to the outputs from said third counter for selectively applying the clock pulse generated by said clock pulse generator to said first and second register groups through said operation control means to act as shift pulses.

4. The apparatus according to claim 3 wherein said operation control means comprises a one-shot generator which operates at the build-down portion of the output from said decoder, a three-bit ring counter connected to receive a shift pulse comprising the output from said one-shot generator, only one bit of said ring counter being at 1 state, an AND gate circuit connected to be enabled when the content of the most significant bit of said ring counter changes to 1 state, a second clock pulse generator for applying a clock pulse to said memory device through said AND gate circuit to act as a shift pulse, a fourth counter for counting the number of clock pulses, through said AND gate circuit of the same number as the number of addresses in one line register of said memory device, and a second one-shot generator which operates at the build-down portion of the carry output from said fourth counter for producing a pulse indicating that writing of the data is said memory device has been completed.

5. An apparatus for selectively segmenting red blood corpuscles and white blood corpuscles of a blood sample comprising:

means for successively illuminating said sample with monochromatic light having a first wavelength between 400 nm and 430 nm and with monochromatic light having a second wavelength between 500 nm and 560 nm, means for detecting light passing through said sample and producing a first detected electrical signal which varies as a function of the intensity of light received at said first wavelength and a second electrical signal which varies as a function of the intensity of light received at said second wavelength, means for comparing said first detected signal with a first electrical threshold signal and producing a first binary signal having one binary value when said first detected signal is above said first threshold signal and the second value when the first detected signal is below said first threshold signal, means for comparing said second detected signal with a second electrical threshold signal and producing a second binary signal having one binary value when said second detected signal is above said second threshold signal and the other binary value when said second detected signal is below said second threshold signal, means for logically combining said first and second binary signals to produce an output indicating whether said second binary signal is produced by illuminating a red or white corpuscle.

6. An apparatus as in claim 5 wherein said logically combining means includes means for carrying out an exclusive OR operation and means for carrying out a product operation.

* * * * *